United States Patent
Kim et al.

(10) Patent No.: US 9,683,060 B2
(45) Date of Patent: Jun. 20, 2017

(54) METHOD FOR PREPARING POLYBUTENE

(71) Applicant: DAELIM INDUSTRIAL CO., LTD., Seoul (KR)

(72) Inventors: Myeong Seok Kim, Sejong (KR); Min Sup Park, Daejeon (KR); Hyung Jae Seo, Daejeon (KR); Se Hyun Lee, Daejeon (KR)

(73) Assignee: DAELIM INDUSTRIAL CO., LTD., Seoul (KR)

( * ) Notice: Subject to any disclaimer, the term of this patent is extended or adjusted under 35 U.S.C. 154(b) by 0 days.

(21) Appl. No.: 14/801,357

(22) Filed: Jul. 16, 2015

(65) Prior Publication Data

US 2015/0322181 A1 Nov. 12, 2015

Related U.S. Application Data

(63) Continuation-in-part of application No. PCT/KR2014/000391, filed on Jan. 14, 2014.

(30) Foreign Application Priority Data

Jan. 17, 2013 (KR) .......................... 10-2013-0005211

(51) Int. Cl.
| | |
|---|---|
| *C08F 10/10* | (2006.01) |
| *C07C 5/13* | (2006.01) |
| *C08F 110/10* | (2006.01) |
| *C10G 45/32* | (2006.01) |
| *C10G 45/58* | (2006.01) |
| *C10G 50/00* | (2006.01) |
| *C10G 69/00* | (2006.01) |
| *C10G 69/12* | (2006.01) |

(52) U.S. Cl.
CPC .............. *C08F 110/10* (2013.01); *C07C 5/13* (2013.01); *C08F 10/10* (2013.01); *C10G 45/32* (2013.01); *C10G 45/58* (2013.01); *C10G 50/00* (2013.01); *C10G 69/00* (2013.01); *C10G 69/126* (2013.01)

(58) Field of Classification Search
CPC .................................... C07C 5/13; C07C 5/22
USPC .......................... 585/253, 259, 670, 809, 841
See application file for complete search history.

(56) References Cited

U.S. PATENT DOCUMENTS

| | | | | |
|---|---|---|---|---|
| 4,435,609 A * | 3/1984 | Gschwendtner | ...... | C07C 5/2556 585/664 |
| 5,012,030 A * | 4/1991 | Lane | .......... | C07C 2/22 585/527 |
| 5,087,780 A * | 2/1992 | Arganbright | .............. | C07C 5/05 585/259 |
| 5,674,955 A * | 10/1997 | Kerr | ...................... | C08F 210/08 526/209 |
| 6,207,115 B1 | 3/2001 | Chodorge et al. | | |
| 6,242,661 B1 * | 6/2001 | Podrebarac | ............. | C07C 7/148 203/29 |
| 6,686,510 B2 * | 2/2004 | Commereuc | ............. | C07C 6/04 585/259 |
| 7,105,616 B2 * | 9/2006 | Auer | ....................... | C08F 6/003 526/133 |
| 7,411,104 B2 * | 8/2008 | Yun | .......................... | C08F 10/08 526/209 |
| 7,888,541 B2 * | 2/2011 | Gartside | ................. | B01D 3/009 585/253 |
| 7,982,086 B2 * | 7/2011 | Almering | ................. | C07C 7/005 203/DIG. 6 |
| 2007/0265483 A1 * | 11/2007 | Himelfarb | .................. | C07C 2/58 585/664 |
| 2009/0023882 A1 * | 1/2009 | Hanefeld | .............. | C08F 110/10 526/348.7 |
| 2010/0234542 A1 * | 9/2010 | Blackborow | ............ | C08F 10/10 526/77 |
| 2010/0298507 A1 * | 11/2010 | Menschig | .............. | C08F 110/10 526/64 |
| 2014/0046110 A1 * | 2/2014 | Iselborn | ..................... | C07C 5/13 585/646 |

FOREIGN PATENT DOCUMENTS

| | | | | |
|---|---|---|---|---|
| CN | 1120049 A | 4/1996 | | |
| CN | 1213970 C | 7/2002 | | |
| EP | 288 362 A1 * | 10/1988 | ............. | C07C 11/08 |
| KR | 10-0140716 B1 | 8/1989 | | |
| KR | 10-1996-0041140 A | 12/1996 | | |
| KR | 10-2002-0029083 A | 4/2002 | | |
| KR | 10-2002-0037083 A | 5/2002 | | |
| KR | 10-2009-0014372 A | 2/2009 | | |
| KR | 10-2010-0069011 A | 6/2010 | | |
| WO | WO 2007/141277 A1 * | 12/2007 | ............. | C08F 10/10 |
| WO | WO 2010/071307 A2 * | 6/2010 | ............. | B01J 31/30 |

OTHER PUBLICATIONS

International Preliminary Report on Patentability dated Jul. 21, 2015 issued in corresponding International Application No. PCT/KR2014/000391.

\* cited by examiner

*Primary Examiner* — Rip A Lee

(74) *Attorney, Agent, or Firm* — Nath, Goldberg & Meyer; Jerald L. Meyer; Tanya E. Harkins

(57) ABSTRACT

Disclosed is a method for preparing a highly reactive polybutene of high quality having low fluorine content and high vinylidene content at high mileage of catalyst with economy. The method for preparing a polybutene includes: performing a selective hydrogenation reaction of diolefin among C4 hydrocarbon components produced from petroleum refineries or naphtha cracking centers, which involve cracking of crude oils, and simultaneously an isomerization reaction of 1-butene to 2-butene and then isolating an isobutene feedstock through fractional distillation; and polymerizing the isobutene feedstock obtained by the fractional distillation.

13 Claims, No Drawings

METHOD FOR PREPARING POLYBUTENE

This is a Continuation-In-Part of International Application No. PCT/KR2014/000391 filed Jan. 14, 2014, an application claiming the benefit to Korean Application No. 10-2013-0005211, filed on Jan. 17, 2013, the content of each of which is hereby incorporated by reference in its entirety.

TECHNICAL FIELD

The present invention relates to a method for preparing a polybutene, and more particularly to a method for preparing a high-quality polybutene having a low fluorine content and a high vinylidene content at high mileage of catalyst with economy.

BACKGROUND ART

Polybutene is a polymer produced from a C4 olefin having 4 carbon atoms formed in the cracking process of hydrocarbons in the presence of a Friedel-Craft type catalyst. The number average molecular weight (Mn) of polybutene is about 300 to 5,000. The feedstock residue remaining after extraction of 1,3-butadiene from C-4 hydrocarbons produced in petroleum refineries or naphtha cracking centers (NCCs) that involve cracking crude oils contains paraffins such as iso-butane or n-butane and olefins, such as 1-butene, 2-butene, isobutene, etc. The isobutene content of the feedstock is approximately 20 to 50 wt. %. The isobutene is mainly used in the preparation of methyl-t-butyl ether (MTBE) used as an octane enhancer, or polybutenes. As the isobutene is the most reactive one of the olefins, the polybutenes are produced mostly from the isobutene units. Conventionally, polybutenes have been used in gluing agents, adhesives or isolating oils, and those with low reactivity are preferred. Such low-reactivity polyisobutylene are called "conventional PIB". In recent years, polybutenes with polar groups are increasingly used in anti-scuff agents for engine oil, viscosity index improvers, or cleansers used in combination with the fuel in the internal combustion engines for automobile or the like. Such highly reactive polyisobutylenes are called "highly reactive polyisobutylene (HR-PIB)".

The most popular one of the products obtained by introducing polar groups to the polybutene is polyisobutylene succinic anhydride (PIBSA) that is prepared by the reaction of polybutene with maleic anhydride. From the PIBSA, a variety of lubricant additives or fuel cleansers are prepared. In the preparation of PIBSA, as the double bond of the polybutene is located at the furthermost end of the polybutene, that is, the polybutene is the highly reactive polyisobutylene (HR-PIB), the polybutene can react directly with the maleic anhydride to form PIBSA with high yield. On the contrary, when the polybutene is a conventional PIB that has a relatively low reactivity due to its double bond positioned inside and many alkyl groups included as substituents causing steric hindrance, it is necessary to chlorinate the polybutene with chlorine gas and put it in the reaction with maleic anhydride to produce PIBSA.

In order to enhance the reactivity of polybutene, the polymerization conditions for polybutene are so controlled as to have the double bond of the polybutene position at the furthermost end of the polybutene as possible. The double bond positioned at the terminal end of polybutene is called "vinylidene". The compound having a vinylidene content of 70% or higher is "highly reactive polyisobutylene", the compound having a vinylidene content of about 40 to 70% is "mid vinylidene polyisobutylene (MV-PIB), and the compound having a vinylidene content of 3 to 40% is a conventional polyisobutylene. The choice of catalysts and cocatalysts is of great importance in the control of the reactivity of the polybutene. Generally, the catalyst is boron trifluoride ($BF_3$) and the cocatalyst is alcohols, ethers, or the like. Further, in the synthesis of a polybutene in which the position of the double bond is not induced to the terminal, aluminum trichloride ($AlCl_3$) is available as a catalyst to obtain a conventional polyisobutylene having a vinylidene content of 3 to 40%. In the preparation of polybutene, the n-butene included in the feedstock possibly causes deterioration in the product quality, the productivity per unit catalyst and the productivity per unit feedstock, but the higher isobutene content of the feedstock leads to an increase in the product quality, the productivity per unit catalyst and the productivity per unit feedstock.

It is particularly desirable to use a high-quality isobutene feedstock removed of n-butene in order to produce a highly reactive polyisobutylene having a high terminal vinylidene content and reduce the fluorine content in the product derived from the catalyst. Even for the production of a conventional polyisobutylene, a high-quality isobutene feedstock removed of n-butene is preferably used in order to lower the chlorine content in the product and enhance the productivity per unit feedstock or unit catalyst. There are known various methods for eliminating 1-butene that most adversely affects the quality of the polybutene among the n-butenes. For example, U.S. Pat. No. 5,674,955 discloses a method of producing polybutenes from a feedstock comprising at least 5 wt. % of 1-butene, which method is characterized in that prior to polymerization, the feedstock is subjected to a pre-treatment step in order to reduce the 1-butene content by at least 20 wt. % and then to a polymerization step using a halogen compound as a catalyst to produce a polybutene with a high vinylidene content and a low halogen content. In this method, however, the isomerized 2-butene may still cause deterioration in the catalytic activity and the mileage of catalyst. U.S. Pat. No. 6,207,115 describes a production of propylenes that includes performing selective hydrogenation of diolefin (Ex. Butadiene) using an olefin conversion unit (OCU) and simultaneously isomerization of 1-butene into 2-butene, polymerization of polybutene, and then metathaesis of 2-butene and an ethylene into propylene. But, this method also involves production of polybutenes in the presence of a large quantity of 2-butene, which results in low mileage of catalyst.

The C4 oil produced in the contact degradation of medium-quality oil during the petroleum refining process and the C4 residue produced in the pyrolysis of naphtha contain 20 to 50 wt. % of 1-butene or 2-butene. The use of the C4 olefin in the production of polybutene may result in high halogen content and low vinylidene content in the polybutene product. Further, a high content of n-butene such as 1-butene, etc. present in the C4 olefin (i.e., feedstock) may cause deterioration in the catalytic activity, the quality of polybutene, or the productivity per unit feedstock. As a solution to this problem, a high-purity isobutene can be used. There are several methods of producing (isolating) isobutenes from the C4 mixture: (1) t-butyl alcohol (TBA) dehydration that combines the hydration reaction and the dehydration reaction; (2) methyl t-butyl ether (MTBE) cracking that includes an addition of methanol to isobutene using an acid catalyst and then a cracking into isobutene; and (3) isobutane dehydrogenation. All of these methods, however, take a high expense to produce (isolate) isobutenes, causing a rise of the polybutene cost.

DISCLOSURE OF INVENTION

It is an object of the present invention to provide a method for preparing a polybutene that enables production of a highly reactive polyisobutylene of high quality having a low content of halogens such as fluorine, etc. and a high terminal vinylidene content at high mileage of catalyst with economy.

It is another object of the present invention to provide a method for preparing a polybutene with good productivity per unit feedstock or unit catalyst.

To achieve the objects of the present invention, there is provided a method for preparing a polybutene that includes: performing a selective hydrogenation reaction of diolefin among C4 hydrocarbon components produced from petroleum refineries or naphtha cracking centers that involve cracking crude oils and simultaneously an isomerization reaction of 1-butene to 2-butene and then isolating an isobutene feedstock through fractional distillation; and polymerizing the isobutene feedstock obtained by the fractional distillation.

EFFECTS OF THE INVENTION

Advantageously, the preparation method of polybutene according to the present invention can produce a highly reactive polyisobutylene of high quality having a low content of halogens such as fluorine, etc. and a high terminal vinylidene content at high mileage of catalyst with economy, relative to the methods of using the C4 hydrocarbon feedstock produced from petroleum refineries or naphtha cracking centers (NCCs), which involve cracking crude oils, without any separate treatment or using a feedstock after a simple process of isomerization of 1-butene to 2-butene.

BEST MODES FOR CARRYING OUT THE INVENTION

Hereinafter, the present invention will be described in further detail.

The method for preparing a polybutene includes: performing a selective hydrogenation reaction of diolefin among C4 hydrocarbon components produced from petroleum refineries or naphtha cracking centers, which involve cracking of crude oils, and simultaneously an isomerization reaction of 1-butene to 2-butene and then isolating an isobutene feedstock through fractional distillation; and polymerizing the isobutene feedstock obtained by the fractional distillation.

The hydrogenation reaction of diolefin is a reaction between the most reactive diolefin component (i.e., 1,3-butadiene) out of the C4 hydrocarbon components and hydrogen to form a n-butene (1-butene and 2-butene) mixture. The isomerization reaction of 1-butene to 2-butene is a hydro-isomerization reaction to convert the 1-butene produced by the conversion of the diolefin and the 1-butene included in the C4 hydrocarbon components into 2-butene. The hydrogenation reaction of diolefin and the isomerization reaction of 1-butene to 2-butene may be performed by supplying a hydrogen gas to the C4 hydrocarbon components in the presence of a metal catalyst. The metal catalyst available in the hydrogenation and hydro-isomerization reactions may include metals in Group 10, such as Ni, Pd, Pt, etc. The metal catalyst may be supported on a supporting material. The used amount of hydrogen depends on the content of diolefin among the C4 hydrocarbon components. Preferably, the used amount of hydrogen is greater than the theoretical stoichiometric quantity required to convert the diolefin to n-butane, preferably a little greater than the theoretical stoichiometric quantity, such as, for example, 1 to 1.2 equivalent weight, preferably 1 to 1.1 equivalent weight with respect to the diolefin. In this regard, when the used amount of hydrogen is excessively large, the diolefin is undesirably converted to n-butane. The temperature for the hydrogenation reaction and the hydro-isomerization reaction is typically 20 to 200° C., preferably 50 to 150° C., more preferably 60 to 150° C. The pressure for the hydrogenation reaction and the hydro-isomerization reaction is typically 0.1 to 5 MPa, preferably 0.5 to 4 MPa, more preferably 0.5 to 3 MPa. The conditions for the hydrogenation reaction and the hydro-isomerization reaction are disclosed in detail in U.S. Pat. No. 6,207,115 and included in this specification as references.

Subsequent to the hydrogenation reaction and the hydro-isomerization reaction of C4 hydrocarbon components, a fractional distillation step is performed to isolate an isobutene feedstock, which is supposed to be used in the polymerization of polybutene. The fractional distillation is a method of isolating a mixture of different liquids with a fractional distillation tower using the difference in the boiling temperature. The isobutene feedstock obtained (i.e., isolated) by the fractional distillation includes isobutenes as a principal component and a trace of 1-butene and 2-butene. The isobutene feedstock is deprived of the most of the n-butene (i.e., 1-butene, etc.) and thus contains relatively highly pure isobutenes. The conditions for fractional distillation to obtain the isobutene feedstock may include the number of the fractioning columns in the fractional distillation tower, the operational temperature, the operational pressure, and so forth. The number of the fractioning columns in the distillation tower for obtaining an isobutene feedstock appropriate to the present invention is in the range of 20 to 150, preferably 50 to 130, more preferably 70 to 130. When the number of the fractioning columns in the distillation tower is less than 20, the isolation efficiency for the feedstock possibly becomes deteriorated to lower the purity of the isobutene (IB). When the number of the fractioning columns in the distillation tower is more than 150, an unnecessary equipment expense occurs. The fractional distillation temperature is 0 to 100° C., preferably 10 to 80° C., more preferably 20 to 80° C. When the fractional distillation temperature is lower than 0° C., there is a rise of the expenses for the vacuum equipment and its accessories. When the fractional distillation temperature is higher than 100° C., it leads to an unnecessary consumption of energy and a rise of the equipment expense for maintaining the high pressure. Above the defined range of the fractional distillation temperature, it may be impossible to obtain a desired highly reactive polyisobutylene of high quality. The fractional distillation pressure is 0 to 30 atm, preferably 2 to 15 atm, more preferably 3 to 10 atm, further more preferably 5 to 10 atm. The fractional distillation pressure approaching zero means vacuum distillation. When the fractional distillation pressure exceeds 30 atm, the boiling point of the mixture rises to consume energy more than needed and the expense for peripheral equipment increases. Further, when the fractional distillation pressure gets out of the defined range, it may possibly lead to a failure to obtain a highly reactive polyisobutylene with high quality. The use of the isobutene feedstock obtained by the fractional distillation to synthesize a polybutene through polymerization can produce a polybutene having high quality (i.e., high vinylidene content and low halogen content) and high efficiency of production as equivalent to those of the polybutene synthesized from a highly pure isobutene. In the following Table 1 is presented an exemplary composition of the isobutene feedstock. It is from isolated under the defined conditions, such as 105 fractioning columns of the distillation tower, distillation temperature of 50° C./60° C. (top/bottom) and distillation pressure of 6 atm and used in the present invention.

TABLE 1

| | Ingredient | | | | | |
|---|---|---|---|---|---|---|
| | Isobutene | n-butane | 1-butene | C-2-butene | T-2-butene | i-butane |
| Content (wt %) | 89.0 | 2.0 | 1.3 | 0.2 | 1.3 | 6.2 |

The use of high content isobutene feedstock in Table 1 to synthesize a polybutene through polymerization can produce polybutene having high polymerization heating and high viscosity, so that the reaction control may be difficult. Therefore, it is desirable to carry out the reaction with adjusting the reaction yield below a certain level, for example less than 70%, preferably less than 60%, more preferably less than 50%. In this case, since the content of unreacted isobutene in C4 mixture after the reaction is high (about 2 to 20 weight %), it is desirable to reuse the C4 mixture after the reaction.

TABLE 2

| | Ingredient | | | | | |
|---|---|---|---|---|---|---|
| | Isobutene | n-butane | 1-butene | C-2-butene | T-2-butene | i-butane |
| Content (wt %) | 53.2 | 0.6 | 1.9 | 0.1 | 0.9 | 43.3 |

TABLE 3

| | Ingredient | | | | | |
|---|---|---|---|---|---|---|
| | Isobutene | n-butane | 1-butene | C-2-butene | T-2-butene | i-butane |
| Content (wt %) | 6.0 | 5.9 | 7.1 | 1.1 | 1.2 | 78.7 |

In order to enhance a production efficiency of polybutene and to easily control the reaction, after reacting the feedstock of Table 1, the unreacted C4 mixture (for example, the mixture of Table 3) is recycled to be diluted, so that C4 mixture (for example, mixture in Table 2) in which isobutene of 25 to 65 wt % is contained and the n-butene component is decreased, is prepared to be used as the feedstock for the polybutene polymerization reaction. The preparation of polybutene by using the C4 mixture (for example, mixture in Table 2) in which isobutene of 25 to 65 wt % is contained and the n-butene component is decreased, results in production of high reactive polybutene having high vinylidene content and a low halogen content, in high yields (about 85 to 95%, the unreacted isobutene content after the reaction is of about 2 to 20%) and high catalyst mileage (polybutene productivity per unit catalyst is about 300~1200 g/mol).

The composition of the C4 residue removed of diolefin and acetylene through the hydrogenation reaction among the C4 hydrocarbon components produced from naphtha cracking centers is presented in the following Table 4. The C4 residue of the composition shown in Table 2 contains a large quantity of n-butene components (1-butene, C (cis)- or T (trans)-2-butene, etc.) and is thus impossible to use in the preparation of highly reactive polyisobutylene having a high vinylidene content and a low halogen content.

TABLE 4

| | Ingredient | | | | | |
|---|---|---|---|---|---|---|
| | Isobutene | n-butane | 1-butene | C-2-butene | T-2-butene | i-butane |
| Content (wt %) | 49.5 | 10.9 | 24.8 | 4.2 | 9.3 | 2.9 |

The composition of the isobutene feedstock (produced simply by isomerization) obtained by removing diolefin and acetylene through a selective hydrogenation reaction using an olefin conversion unit (OCU) and isomerizing 1-butene to 2-butene is presented in the following Table 5.

TABLE 5

| | Ingredient | | | | | |
|---|---|---|---|---|---|---|
| | Isobutene | n-butane | 1-butene | C-2-butene | T-2-butene | i-butane |
| Content (wt %) | 44.9 | 10.9 | 1.7 | 14.2 | 23.4 | 4.9 |

Subsequently, the isobutene thus produced (isolated) as above is polymerized according to a general method to form a polybutene. The method of producing a polybutene from the isobutene feedstock can be classified into a method of producing a conventional polyisobutylene using aluminum trichloride ($AlCl_3$) as a catalyst and a method of producing a highly reactive polyisobutylene and a med vinylidene polyisobutylene using boron trifluoride ($BF_3$) as a catalyst and a cocatalyst. The method of producing a conventional polyisobutylene using aluminum trichloride ($AlCl_3$) as a catalyst is widely known. Hence, a brief description will be given as to the method of producing a highly reactive polyisobutylene in the presence of boron trifluoride ($BF_3$) as a catalyst.

In the preparation of a highly reactive polyisobutylene, both a cocatalyst (i.e., alcohol, ether, etc.) and boron trifluoride ($BF_3$) may be added directly into a reactor or produced in the form of a complex in a separate tank and then put into a reactor. The alcohol compound used as the cocatalyst may be a primary, secondary or tertiary alcohol having 1 to 4 carbon atoms, such as, for example, methanol, ethanol, isopropanol, n-propanol, isobutanol, t-butanol, etc. The ether compound used as the cocatalyst may be a primary, secondary or tertiary ether having 2 to 8 carbon atoms, such as, for example, dimethyl ether, diethyl ether, diisopropyl ether, methylpropyl ether, methylisopropyl ether, methylethyl ether, methylbutyl ether, methyl-t-butyl ether, ethylpropyl ether, ethylisopropyl ether, ethylbutyl ether, ethylisobutyl ether, ethyl-t-butyl ether, etc. The cocatalyst may be used alone or in combination with at least one of other cocatalysts. In forming a complex of the cocatalyst and boron trifluoride, the cocatalyst alone or in combination with at least one of other cocatalysts is added into a tank, and a boron trifluoride gas is then added to easily produce a complex. In this regard, the reaction of forming a complex of boron trifluoride and alcohol is an exothermic reaction. It is therefore desirable to eliminate the heat of reaction in order to reduce the risk of catalyst decomposition and explosion. Particularly, for the sake of completely eliminating the heat of reaction to maintain the stability of the catalyst, the complex reaction is performed at a low temperature, preferably 10° C. or below, more preferably 0° C. or below, most preferably −40° C. to −10° C. The used amount of the catalyst is desirably controlled so that the content of boron trifluoride in the catalyst component is 0.05 to 1.0 part by weight with respect to 100 parts by weight of the isobutene in the isobutene feedstock. When the used amount of boron trifluoride is greater than 1.0 part by weight, it may lead to the formation of a product having an excessively low molecular weight and the deterioration of productivity per catalyst, consequently with poor economy. When the used amount of boron trifluoride is less than 0.05 part by weight, the yield of polybutene is deteriorated, which is undesirable in the aspect of economy.

On the other hand, the method for preparing the polybutene according to the present invention, in order to enhance the use efficiency of isobutene feedstock, may comprise a step of recycling whole or part of unreacted isobutene feedstock (for example, material containing components shown in Table 3) which is recovered from C4 distillation column after the polybutene polymerization reaction, to the isomerization step and/or the polybutene polymerization step, thereby dilute the isobutene feedstock. For example, whole or part of unreacted isobutene feedstock is recycled to the polybutene polymerization step so that the high concentrated isobutene feedstock which is obtained in the isomerization step may be diluted or recycled to the isomerization step again. In the method for preparing polybutene according to the present invention, the concentration of isobutene in the isobutene feedstock or diluted isobutene feedstock is 25 to 65 wt %, preferably 30 to 60 wt %, and the isobutene content in the unreacted isobutene feedstock after the polybutene polymerization reaction is preferably 2 to 20 wt %. The reason to low the content (concentration) of isobutene in C4 mixture by diluting the isobutene feedstock is that when the isobutene content is too high, it is difficult to control the reaction heat generated in the polybutene polymerization reaction with a heat exchanger. On the other hand, when the isobutene feedstock is excessively diluted, the isobutene content in the C4 mixture is unduly reduced, and as well as the preparation of polybutene having high molecular weight is difficult, but also the production yield and economic efficiency of the polybutene are lowered.

Since organic substance of alcohol or ether containing oxygen (O) atoms, a halogen acid and the like, may be included in the recycling feedstock (that is, unreacted C4), it is desirable to remove these substances. The adsorbing tower charged with a adsorbent can be used for removing the organic substance and halogen acid. Examples of the absorbent include $Ca(OH)_2$, CaO, $CaCO_3$, $CaCl_2$, KOH, $K_2CO_3$, $KHCO_3$, KCl, NaOH, $Na_2CO_3$, $NaHCO_3$, solid silica, solid alumina, zeolite, anion exchange resin to which amine group is bonded, cation exchange resin to which sulfono group is bonded and so on. It is preferable to use among them, $Ca(OH)_2$, CaO, $CaCO_3$, $CaCl_2$, solid silica, solid alumina or resins in which halide ions (X−), for example, fluoride ion (F−) is absorbed and is insoluble in water. The adsorbing tower for removing the organic substance of alcohol, ether containing oxygen (O) atoms and the absorbing tower for removing the halogen acid are respectively mounted to enhance impurity removal effects and plant operational efficiency.

The sorbent should have a suitable particle size, for example 0.1 to 100 mm, preferably 0.5 to 100 mm, more preferably 1 to 100 mm (diameter), so as to fix the catalyst and facilitate application to a tubular fixed-bed reactor. When the diameter of the sorbent is less than 0.1 mm, application to the tubular fixed-bed reactor may be difficult, and when the diameter of the sorbent is more than 100 mm, the absorption efficiency may be lowered. The adsorbent particles may be processed (molded) in a constant form, for example, spherical form, cylindrical form, tablet-shaped, preferably. the adsorbent particles may be processed in spherical form. When CSTR (Stirred-Tank Reactor), a type of MFR (Mixed Flow Reactor) is used, all kinds of catalyst can be used, however, the fine powder is likely to remain in the reactor.

In case where the general polybutene or high reactive polybutene (for example, high reactive polybutene having vinylidene content of 80 mol % or more and the conversion ratio of isobutene of 85% or more) is prepared with a conventional preparing method (using aluminum trichloride catalyst or a boron trifluoride complex catalysts and using C4 mixture containing high content isobutene as the reaction material), the material cost is too high and there is a disadvantage that the product cost increases. However when C4 mixture containing isobutene which is obtained by the process according to the present invention is used as the reaction material, polybutene having quality similar to when high-purity expensive isobutene is used, can be economically prepared.

As for the highly reactive polyisobutylene, the polymerization (reaction) temperature is generally −30° C. to 20° C., and the polymerization (reaction) pressure is determined to maintain the isobutene feedstock in the liquid state at the corresponding reaction temperature, that is, typically 3 $kg/cm^2$ or higher. Generally, the conversion rate of isobutene is at least 70%, more preferably about 80 to 95%. In the present invention, the retention time required to achieve the above conversion rate is generally 5 to 100 minutes. The retention time out of the defined range is undesirable in the aspect of economy. Upon the completion of the polybutene polymerization, the subsequent process such as neutralization typically adopted in the related art is carried out to complete a highly reactive polyisobutylene. The highly reactive polyisobutylene prepared according to the present invention has a number average molecular weight (Mn) of 300 to 5,000, a vinylidene content of at least 80% and an isobutene conversion rate of at least 85%.

The preparation method for polybutene according to the present invention makes it possible to perform a polymerization with efficiency that leads to the production of not only a highly reactive polyisobutylene having a vinylidene (i.e., a double bond (vinylidene) positioned at the terminal of the polybutene among the total double bonds present in the polybutene) content of at least 70% but also a mid-vinylidene polyisobutylene having a vinylidene content of about 40 to 70% and/or a conventional polyisobutylene having a vinylidene content of 3 to 40%. In the preparation of polybutenes, particularly highly reactive polybutenes having a vinylidene content of at least 80% and an isobutene conversion rate of at least 85%, the expense of the feedstock is so extremely increased as to yield uncompetitive products when using a typical boron trifluoride complex catalyst and a general isolation method to separate high-purity isobutene. However, the use of the isobutene feedstock isolated according to the present invention in the preparation of polybutene can produce high-quality polybutenes having a low fluorine content and a high vinylidene content at high mileage of catalyst with economy.

As the C4 oil produced in the contact degradation of medium-quality oil and the C4 residue produced in the pyrolysis of naphtha during the petroleum refining process contain 20 to 40 wt. %, specifically 20 to 35 wt. % of n-butene (i.e., 1-butene, etc.), the productivity and quality of the polybutene product may deteriorate (i.e., having a low vinylidene content and a high halogen content). However, the preparation method for polybutene according to the present invention uses a feedstock removed of the n-butene components that possibly deteriorate the quality and productivity of the product, thereby solving the above-mentioned problems. Further advantageously, the highly reactive polybutene having a high vinylidene content as prepared according to the present invention not only displays the higher content of the effective ingredients having a cleansing function in the preparation of lubricants, fuel cleansers, etc. but also has the lower halogen content, which may prevent corrosion of the reactant possibly occurring in the preparation of additives for fuel cleansers or lubricants.

Hereinafter, the present invention will be described in further detail with reference to the following examples and comparative examples, which are given for the understanding of the present invention and not intended to limit the scope of the present invention.

[Examples 1 to 4] Preparation of Highly Reactive Polybutene

Out of the C4 hydrocarbon feedstock produced in the petroleum refining facilities or the naphtha cracking centers (NCCs) that involve cracking of crude oils, diolefin (i.e., butadiene) is selectively hydrogenated, and simultaneously, 1-butene is isomerized to 2-butene. Then, a fractional distillation process (105 fractioning columns in the fractional distillation tower, distillation temperature of 50° C./60° C. (top/bottom), and distillation pressure of 6 atm) is performed to obtain an isobutene feedstock having a composition as presented in Table 1. The isobutene feedstock having the composition of Table 1 is consecutively fed into a stainless pressure reactor equipped with a cooling apparatus and then subjected to polymerization using the polymerization temperature (reaction temperature), catalyst (BF3) and cocatalyst (e.g., ethanol, ethanol, or diisopropyl ether (IPE)) as presented in Table 4 to produce a polybutene (Examples 1 to 4). In this regard, the pressure of the reactor is maintained at 3 kg/cm2 or higher in order to keep the isobutene feedstock in the liquid state. The average retention time is 30 minutes. After 180 minutes, the polymer liquid is collected from the outlet of the reactor directly into a container filled with a solution containing 5 wt. % of caustic soda, mixed with an approximately 3-fold volume of hexane and then washed with water three times to eliminate the unreacted feedstock and the solvent. Finally, a 30-minute stripping process is carried out at 220° C. and 5 mmHg to remove the remaining component of low boiling temperature, thereby obtaining polybutenes as the target products. The final products are measured in regards to molecular weight (number average molecular weight, Mn) and molecular weight distribution (MWD) using the gel permeation chromatography (GPC) method. Further, the vinylidene content (%) is analyzed using the C13-NMR, and the F content (ppm) is determined using the ion selective electrode (ISE) method. The measurement results are presented in Table 6. In the Table 6, "after-reaction IB content (%)" and "IB conversion rate (%)" are determined by the comparison of the isobutene (IB) content before and after the reaction through gas chromatography (GC) analysis to analyze the reaction participation level of the isobutene (IB).

[Comparative Examples 1 and 2] Preparation of Highly Reactive Polybutene

The C4 hydrocarbon feedstock produced from the naphtha cracking center (NCC) is removed of butadiene to obtain a C4 residue-1 (raffinate-1) having a composition as presented in Table 2 and then used as an isobutene feedstock. The isobutene feedstock having the composition of Table 2 is consecutively fed into a stainless pressure reactor equipped with a cooling apparatus and then subjected to polymerization using the polymerization temperature (reaction temperature), catalyst ($BF_3$) and cocatalyst (e.g., ethanol, ethanol, or diisopropyl ether (IPE)) as presented in Table 4 to produce polybutenes (Comparative Examples 1 and 2). The other conditions are the same as described in Examples 1 to 4. The polybutenes thus obtained are analyzed in regards to molecular weight (number average molecular weight, Mn), molecular weight distribution (MWD), vinylidene content (%), F content (ppm), after-reaction IB content (%), IB conversion rate, and mileage of catalyst (PIB/$BF_3$) in the same manner as described in Examples 1 to 4. The measurement results are presented in Table 4.

[Comparative Examples 3 and 4] Preparation of Highly Reactive Polybutene

Out of the C4 hydrocarbon feedstock produced from the petroleum refining facilities or the naphtha cracking centers (NCCs) that involve cracking crude oils, diolefin (i.e., butadiene) is selectively hydrogenated, and simultaneously, 1-butene is simply isomerized to 2-butene to obtain an isobutene feedstock having a composition of Table 3. The isobutene feedstock having the composition of Table 3 is consecutively fed into a stainless pressure reactor equipped with a cooling apparatus and then subjected to polymerization using the polymerization temperature (reaction temperature), catalyst ($BF_3$) and cocatalyst (e.g., ethanol, ethanol, or diisopropyl ether (IPE)) as presented in Table 4 to produce polybutenes (Comparative Examples 3 and 4). The other conditions are the same as described in Examples 1 to 4. The polybutenes thus obtained are analyzed in regards to molecular weight (number average molecular weight, Mn), molecular weight distribution (MWD), vinylidene content (%), F content (ppm), after-reaction IB content (%), IB conversion rate, and mileage of catalyst (PIB/$BF_3$) in the same manner as described in Examples 1 to 4. The measurement results are presented in Table 6.

TABLE 6

|  | Example 1 | Example 2 | Example 3 | Example 4 | Comparative Example 1 | Comparative Example 2 | Comparative Example 3 | Comparative Example 4 |
| --- | --- | --- | --- | --- | --- | --- | --- | --- |
| Methanol | 1.70 |  | 1.0 |  |  |  | 1.7 |  |
| Ethanol |  | 1.65 |  | 1.0 | 1.65 | 2.0 |  | 1.65 |
| IPE |  |  | 0.6 | 0.4 |  |  |  |  |
| Cocatalyst/$BF_3$ Mole Ratio | 1.7 | 1.65 | 1.60 | 1.40 | 1.65 | 2.0 | 1.7 | 1.65 |
| After-reaction IB content (%) | 7.5 | 8.6 | 9.0 | 5.1 | 14.6 | 14.3 | 8.2 | 8.4 |

TABLE 6-continued

|  | Example 1 | Example 2 | Example 3 | Example 4 | Comparative Example 1 | Comparative Example 2 | Comparative Example 3 | Comparative Example 4 |
|---|---|---|---|---|---|---|---|---|
| IB conversion rate (%) | 93 | 92 | 91 | 95 | 83 | 83 | 92 | 92 |
| Reaction temperature (° C.) | −25 | −25 | −18 | −18 | −25 | −25 | −25 | −25 |
| Mileage of catalyst (PIB/BF$_3$) | 634 | 610 | 603 | 961 | 412 | 162 | 240 | 266 |
| Vinyldene (%) | 88.3 | 89.3 | 90.5 | 89.2 | 80.2 | 85.6 | 86.0 | 87.8 |
| F(ppm) | 6 | 4 | 3 | 4 | 41 | 31 | 5 | 4 |
| Mn(MWD) | 1830 (1.85) | 2350 (1.90) | 1060 (1.34) | 1370 (1.47) | 2250 (1.88) | 1270 (1.55) | 1980 (1.79) | 2410 (1.88) |

In Table 6, "cocatalyst/BF$_3$" indicates the ratio of the total moles of cocatalyst to the moles of BF$_3$. As can be seen from Table 6, the polybutenes prepared according to the Examples 1 to 4 of the present invention have a vinylidene content of at least 88% (the higher, the better) and a F content of 10 ppm or less (the lower, the better), which satisfy the high-quality and high-reactivity standards. On the contrary, when using the C4 residue-1 feedstock as in the Comparative Examples 1 and 2, the feedstock expense is low, but the used amounts of the catalyst and cocatalyst are too large and the product yield is low, causing a rise of the product cost and deterioration in the properties of the polybutene products. In addition, when using the isobutene feedstock obtained simply by isomerization as in the Comparative Examples 3 and 4, it may be possible to produce polybutenes with good quality to some degree, but the extremely low mileage of catalyst undesirably leads to low productivity.

What is claimed is:

1. A method for preparing a polybutene, comprising:
performing a selective hydrogenation reaction of diolefin among C4 hydrocarbon components produced from petroleum refineries or naphtha cracking centers, which involve cracking crude oils, and simultaneously an isomerization reaction of 1-butene to 2-butene and then isolating an isobutene feedstock through fractional distillation;
polymerizing the isobutene feedstock in the presence of a polymerization catalyst to prepare the polybutene; and
recycling whole or part of unreacted isobutene feedstock, after the polymerization ion reaction, to the isomerization step thereby diluting the isobutene feedstock.

2. The method for preparing a polybutene as claimed in claim 1, wherein the isobutene content in the isobutene feedstock or diluted isobutene feedstock is 25 to 65 wt %.

3. The method for preparing a polybutene as claimed in claim 1, wherein the isobutene content in the unreacted isobutene feedstock, after the polybutene polymerization reaction, is 2 to 20 wt %.

4. The method for preparing a polybutene as claimed in claim 1, wherein a product from the polybutene polymerization reaction is a conventional polybutene in which vinylidene positioned at the terminal of the polybutene is 70% or less, and the polymerization catalyst is aluminum trichloride.

5. The method for preparing a polybutene as claimed in claim 1, wherein a product from the polybutene polymerization reaction is a high reactive polybutene in which vinylidene positioned at the terminal of the polybutene is more than 70% and whose number average molecular weight (Mn) is 300 to 5,000, and the polymerization catalyst includes boron trifluoride (BF$_3$) and a cocatalyst.

6. The method for preparing a polybutene as claimed in claim 5, wherein the cocatalyst is a primary, secondary or tertiary alcohol having 1 to 4 carbon atoms or a primary, secondary or tertiary ether having 2 to 8 carbon atoms.

7. The method for preparing a polybutene as claimed in claim 1, further comprising a step of removing an organic substance containing oxygen (O) atoms and a halogen acid from the recycling unreacted isobutene feedstock.

8. The method for preparing a polybutene as claimed in claim 7, wherein the removal of the organic substance containing oxygen (O) atoms and halogen acid is carried out by making the recycling unreacted isobutene feedstock pass through an adsorbing tower charged with a adsorbent, and wherein the absorbent is one selected from the group consisting of Ca(OH)$_2$, CaO, CaCO$_3$, CaCl$_2$, KOH, K$_2$CO$_3$, KHCO$_3$, KCl, NaOH, Na$_2$CO$_3$, NaHCO$_3$, solid silica, solid alumina, zeolite, anion exchange resin to which amine group is bonded, cation exchange resin to which sulfono-group is bonded and mixtures thereof.

9. The method for preparing a polybutene as claimed in claim 8, wherein an adsorbing tower for removing the organic substance containing oxygen (O) atoms and an absorbing tower for removing the halogen acid are respectively mounted.

10. The method for preparing a polybutene as claimed in claim 1, the polymerization temperature is −30 to 20° C., the polymerization pressure is 3 kg/cm$^2$ or above and the retention time is 5 to 100 minutes.

11. The method for preparing a polybutene as claimed in claim 1, wherein the hydrogenation reaction of diolefin and the isomerization reaction of 1-butene are performed by supplying a hydrogen gas to the C4 hydrocarbon component in the presence of a metal catalyst.

12. The method for preparing a polybutene as claimed in claim 1, wherein the fractional distillation step includes isolating the isobutene feedstock with 20 to 150 distillation columns under a fractional distillation temperature of 20 to 80° C. and a fractional distillation pressure of 2 to 10 atm.

13. The method for preparing a polybutene as claimed in claim 1, further comprising a step of recycling part of the unreacted isobutene feedstock to the polybutene polymerization step.

* * * * *